United States Patent [19]
Ueoka et al.

[11] Patent Number: 6,049,013
[45] Date of Patent: Apr. 11, 2000

[54] METHOD FOR PRODUCING ALCOHOL

[75] Inventors: Hideaki Ueoka; Osamu Tabata, both of Wakayama; Tohru Sakamoto, Wayama, all of Japan

[73] Assignee: Kao Corporation, Tokyo, Japan

[21] Appl. No.: 09/030,013

[22] Filed: Feb. 25, 1998

[30] Foreign Application Priority Data

Mar. 3, 1997 [JP] Japan .................................. 9-065463

[51] Int. Cl.$^7$ .................................................. C07C 27/10
[52] U.S. Cl. ............................................................ 568/700
[58] Field of Search .................................. 568/700, 885, 568/814, 836, 877

[56] References Cited

U.S. PATENT DOCUMENTS

| | | | |
|---|---|---|---|
| 5,157,168 | 10/1992 | Wilmott et al. | 568/885 |
| 5,233,099 | 8/1993 | Tabata et al. | 568/885 |
| 5,233,100 | 8/1993 | Tabata et al. | 568/885 |

FOREIGN PATENT DOCUMENTS

| | | |
|---|---|---|
| 0 656 335 | 6/1995 | European Pat. Off. . |
| 0 656 338 | 6/1995 | European Pat. Off. . |
| 41 43 085 | 7/1992 | Germany . |
| 41 43 091 | 7/1992 | Germany . |

OTHER PUBLICATIONS

Database WPI, Derwent Publications, JP 7–188077, Jul. 25, 1995.

Database WPI, Derwent Publications, JP 4–504408, Aug. 6, 1992.

*Primary Examiner*—Louise N. Leary
*Attorney, Agent, or Firm*—Oblon, Spivak, McClelland, Maier & Neustadt, P.C.

[57] ABSTRACT

A method for producing an alcohol including the steps of continuously supplying and flowing starting materials of an alcohol in a reducing reactor; and carrying out catalytic reduction reaction of the starting materials with hydrogen gas in the presence of a hydrogenation catalyst. In this method, the catalytic reduction reaction of the starting materials is carried out under temperature conditions of not less than a dew point of the resulting alcohol, and the starting materials of an alcohol are brought in contact with hydrogen gas in the presence of a hydrogenation catalyst, in which at least one substance selected from the group consisting of starting materials of an alcohol, alcohols, wax esters, and hydrocarbons is present in a liquid form on a surface or within pores of the hydrogenation catalyst.

7 Claims, No Drawings

METHOD FOR PRODUCING ALCOHOL

BACKGROUND OF THE INVENTION

1. Field of the Invention

The present invention relates to a method for producing an alcohol. More specifically, it relates to a method for producing an alcohol comprising continuously supplying and flowing starting materials of an alcohol in the presence of a hydrogenation catalyst and carrying out catalytic reduction reaction of the starting materials to give an alcohol.

2. Discussion of the Related Art

Methods for producing alcohols comprising carrying out reduction reaction of starting materials of an alcohol, such as a fatty acid ester, a fatty acid triglyceride, and a fatty acid, in the presence of a hydrogenation catalyst have been generally carried out under conditions of a pressure of from 200 to 300 atm. and a temperature of from 200° to 300° C. In view of carrying out such methods in an actual production plant, however, a process at such a high pressure necessitates not only equipments with sufficient pressure resistance but also sufficient maintenance of the equipments for keeping air-tightness. Therefore, such equipments would require both of high plant investments and high running costs.

In order to overcome these problems and produce more inexpensive alcohols, various studies have been recently made on the methods for hydrogenation reaction at a relatively low pressure. The methods are disclosed, for instance, in U.S. Pat. No. 5,475,159, Japanese Patent Unexamined Publication No. Hei 4-504408, and Japanese Patent Laid-Open No. Hei 7-188077.

U.S. Pat. No. 5,475,159 discloses a method for producing an aliphatic alcohol comprising hydrogenating a methyl ester of a fatty acid in a liquid-phase reaction under the conditions of a reaction pressure of from 300 to 2000 psig and a reaction temperature of from 170° to 250° C.

Under the above-mentioned conditions, however, a reaction intermediate, a wax ester, is included in a large amount at the outlet of the reactor, and hence, the yield of alcohol is liable to be lowered.

The reasons for a low yield of alcohol are presumably as follows: In the hydrogenation reaction, the amount of hydrogen dissolved in an ester constituting a liquid phase in the reaction system is decreased as the reaction pressure is decreased, thereby drastically lowering the reaction activity. In addition, the chemical reaction during production of an alcohol is an equilibrium reaction, wherein the reaction equilibrium is shifted towards the side where the reaction intermediate, the wax ester, remains in the resulting alcohol under the given pressure conditions mentioned above.

In addition, there are advantages in that since the wax ester has a different boiling point from the formed alcohol and thus can be easily separated by distillation, the lowering in the yield of the alcohol can be prevented, and that the wax ester can be employed again in the hydrogenation process as a starting material for an alcohol after separation and collection of the wax ester. There is, however, a defect in necessitating a plant investment for the separation and collection processes.

On the other hand, Japanese Patent Unexamined Publication No. Hei 4-504408 discloses a method for producing an aliphatic alcohol comprising hydrogenating a lower alkyl ester of a fatty acid in a vapor-phase reaction under the conditions of a reaction pressure of from 5 to 100 bar, a reaction temperature of from 140° to 240° C., and a molar ratio of hydrogen to ester of from 200:1 to 2000:1, wherein a mixture of the ester and hydrogen gas brought into contact with a hydrogenation catalyst is constantly at a temperature higher than its dew point. In addition, Japanese Patent Laid-Open No. Hei 7-188077 discloses a method for producing alcohols comprising the step of hydrogenating esters in a vapor-phase reaction under the conditions of a reaction pressure of from 150 to 2000 psia, a reaction temperature of from 150 to 350° C., and a molar ratio of hydrogen of from 10 to 8000, wherein the temperature conditions are such that the starting material stream is fed at a temperature higher than its dew point by not less than 5° C.

By carrying out the hydrogenation reaction in the vapor phase under the above-mentioned conditions, the conventional problem regarding the amount of hydrogen gas dissolved in the liquid phase under low pressure conditions can be solved, and thereby the reaction activity is remarkably improved. Moreover, since the reaction equilibrium during the production of alcohols is largely shifted toward the side of formation of alcohols in the vapor phase, the amount of the wax ester included in the resulting alcohols at the outlet of the reactor can be expected to be decreased.

Actually, however, a side reaction, namely, the reduction reaction of alcohols to hydrocarbons, is also accelerated, which results in poor selectivity though having excellent reactivity, and hence, the yield is rather notably decreased.

Additionally, in the case where an ester having 8 to 18 carbon atoms is hydrogenated under the above-mentioned conditions, the boiling point region of a hydrocarbon formed as a side-product overlaps with that of a short chain aliphatic alcohol, and hence, it is made difficult to separate the hydrocarbons from the alcohol in the subsequent processes by distillation. Therefore, in order to carry out hydrogenation reaction under the above-mentioned conditions, separation of a short chain fraction from a long chain fraction in the ester prior to the hydrogenation reaction is necessitated.

Accordingly, one object of the present invention is to provide a method for producing an alcohol comprising carrying out catalytic reduction reaction of starting materials of an alcohol in the presence of a hydrogenation catalyst, wherein the method can be carried out without necessitating a step of separating the starting materials depending upon the chain length prior to the reduction reaction, and having excellent reactivity and selectivity even at a low reaction pressure; and specifically, to provide a method for producing an alcohol wherein the amounts of the starting materials of an alcohol remaining unreacted, the reaction intermediate, the wax ester, and the side-products, the hydrocarbons, included in the resulting alcohol are lowered to such an extent that a purification process such as distillation is not necessitated, and thereby making it possible to improve the yield of the alcohol.

These and other objects of the present invention will be apparent from the following description.

SUMMARY OF THE INVENTION

Specifically, the present invention pertains to the method for producing an alcohol comprising the steps of:

continuously supplying and flowing starting materials of an alcohol in a reducing reactor; and carrying out catalytic reduction reaction of the starting materials with hydrogen gas in the presence of a hydrogenation catalyst, wherein the catalytic reduction reaction of the starting materials is carried out under temperature conditions of not less than a dew point of the resulting alcohol, and wherein the starting materials of an alcohol are brought in contact with hydrogen gas in the presence of a hydrogenation catalyst, in which at least one substance selected from the group consisting of starting materials of an alcohol, alcohols, wax esters, and hydrocarbons is present in a liquid form on a surface or within pores of the hydrogenation catalyst.

DETAILED DESCRIPTION OF THE INVENTION

According to the method for producing an alcohol of the present invention, as described above, in the production of an alcohol, when the starting materials of an alcohol are continuously introduced in a reducing reactor and the starting materials are subjected to catalytic reduction reaction with hydrogen gas in the presence of a hydrogenation catalyst, the catalytic reduction reaction of the starting materials is carried out under temperature conditions of not less than a dew point of the resulting alcohol, and the starting materials of an alcohol are brought in contact with hydrogen gas in the presence of a hydrogenation catalyst, in which at least one substance selected from the group consisting of starting materials of an alcohol, alcohols, wax esters, and hydrocarbons is present in a liquid form on surfaces or within pores of the hydrogenation catalyst, to give an alcohol.

Incidentally, in the present specification, the dew point of an alcohol refers a temperature at which a pressure $P_1$, a partial pressure of an alcohol vapor in a reducing reactor, is a saturation vapor pressure for an alcohol. In addition, the dew point of a wax ester refers to a temperature at which a pressure $P_2$, a partial pressure of a wax ester vapor in a reducing reactor, is a saturation vapor pressure for a wax ester.

In the present invention, the starting materials of an alcohol used in the hydrogenation reaction include, for instance, fatty acid esters, and fatty acids. Among them, from the aspect of durability of the hydrogenation catalysts, the fatty acid esters can be preferably used.

Among the fatty acid esters or fatty acids mentioned above, those components derived from coconut oil, palm oil, or palm kernel oil are desirably used in the present invention from the viewpoint of easy availability.

The above-mentioned fatty acid esters are not particularly limited, and examples thereof include, for instance, fatty acid esters wherein an alcohol constituting the fatty acid esters has one or more carbon atoms, a fatty acid constituting the fatty acid esters is saturated or unsaturated having a linear or branched chain, and one or more ester bonds are contained in the ester molecule. Further, alicyclic carboxylic acid esters and aromatic carboxylic acid esters may also be used.

The alcohols, the starting materials of the above-mentioned fatty acid esters, are not particularly limited, and examples thereof include, for instance, methanol, ethanol, 1-propanol, 2-propanol, 1-butanol, 2-butanol, 2-ethylhexanol, 2,2-dimethyl-1,3-propanediol, ethylene glycol, propylene glycol, 1,4-butanediol, 1,6-hexanediol, 1,10-decanediol, cyclohexanol, benzyl alcohol, diethylene glycol, glycerol, and trimethylolpropane.

The fatty acids, the starting materials of the above-mentioned fatty acid esters, are not particularly limited, and examples thereof include, for instance, formic acid, acetic acid, caproic acid, caprylic acid, capric acid, lauric acid, myristic acid, palmitic acid, stearic acid, isostearic acid, oleic acid, oxalic acid, maleic acid, adipic acid, sebacic acid, cyclohexanecarboxylic acid, benzoic acid, phthalic acid, animal (bovine, porcine)-derived fatty acids, and plant (coconut, palm, palm kernel)-derived fatty acids.

Concrete examples of the above-mentioned fatty acid esters include, for instance, methyl esters, such as methyl caproate, methyl caprylate, methyl caprate, methyl laurate, methyl myristate, methyl palmitate, and methyl stearate, and ethyl esters, such as ethyl caproate, ethyl caprylate, ethyl caprate, ethyl laurate, ethyl myristate, ethyl palmitate, and ethyl stearate. These fatty acid esters can be used alone or in admixture of two or more kinds.

Concrete examples of the above-mentioned fatty acids, which may be the same ones listed as the fatty acids for the starting materials of the above-mentioned fatty acid esters, include, for instance, formic acid, acetic acid, caproic acid, caprylic acid, capric acid, lauric acid, myristic acid, palmitic acid, stearic acid, isostearic acid, oleic acid, oxalic acid, maleic acid, adipic acid, sebacic acid, cyclohexanecarboxylic acid, benzoic acid, phthalic acid, and the like. Among these fatty acids, capric acid, lauric acid, myristic acid, palmitic acid, stearic acid, and the like can be desirably used in the present invention. Particularly, lauric acid-containing fatty acids derived from coconut oil, palm oil, or palm kernel oil are preferred in the present invention because of a remarkable improvement in catalytic activities. The above-mentioned fatty acid esters and fatty acids can be used alone or in admixture of two or more kinds.

The hydrogenation catalyst used in the present invention is not particularly limited, and any catalysts known in the art used for hydrogenation reaction can be used without particular limitations. Concrete examples of the hydrogenation catalysts include, for instance, the copper-containing hydrogenation catalysts, such as Cu—Cr, Cu—Zn, Cu—Si, Cu—Fe—Al, and Cu—Zn—Ti. The shapes of the above-mentioned hydrogenation catalyst cannot be absolutely determined because they differ depending on the types of the reactors, and they may be suitably selected from powdery, granular, tablet or other forms.

In the present invention, as the above-mentioned hydrogenation catalysts, there can be used hydrogenation catalysts in which at least one substance selected from the group consisting of starting materials of an alcohol, alcohols, wax esters, and hydrocarbons is present in a liquid form on surfaces or within pores of the hydrogenation catalysts.

As described above, one of the features of the present invention resides in that catalytic reduction reaction is carried out by using a hydrogenation catalyst treated such that at least one substance selected from the group consisting of starting materials of an alcohol, alcohols, wax esters, and hydrocarbons is present in a liquid form on surfaces or within pores of the hydrogenation catalyst.

In other words, when the reaction is carried out under such conditions that the surfaces or the pores of the above-mentioned hydrogenation catalysts are in a dry state, an alcohol can be obtained without substantially forming a wax ester. However, since the formed alcohol can be easily reduced to a hydrocarbon on the surfaces or within the pores of the hydrogenation catalyst, the yield of an alcohol is lowered.

On the contrary, when a hydrogenation catalyst is treated such that the above substance is present in a liquid form on the surfaces or within the pores of the hydrogenation catalyst, the surfaces or the pores of the hydrogenation catalyst are packed with the wax esters formed by the liquid-phase reaction, so that hydrogenation progresses from a wax ester to an alcohol. Moreover, since the formed alcohol is shifted to a vapor phase, a reduction of alcohols to hydrocarbons can be suppressed. Incidentally, in this case, a very small amount of a wax ester is included in the formed alcohol, to an extent that its quality is not mal-affected.

Examples of the above-mentioned alcohols include, for instance, methanol, ethanol, caproyl alcohol, caprylyl alcohol, capryl alcohol, lauryl alcohol, myristyl alcohol, cetyl alcohol, stearyl alcohol, isostearyl alcohol, oleyl alcohol, ethylene glycol, 1,4-butanediol, 1,6-hexanediol, 1,10-decanediol, cyclohexylmethanol, benzyl alcohol, 1,2-benzenedimethanol, and the like. These alcohols can be used alone or in admixture of two or more kinds.

The term "wax ester" used herein refers to a fatty acid ester having a comparatively large molecular weight formed by esterification or transesterification between the alcohol formed by catalytic reduction reaction of the starting materials of an alcohol using a hydrogenation catalyst and the starting materials of an alcohol. In the above wax ester, further hydrogenation reaction progresses depending upon the reaction conditions, to give an alcohol. Examples of the above-mentioned wax esters include, for instance, hexyl caproate, octyl caprylate, decyl caprate, dodecyl laurate, tetradecyl myristate, hexadecyl palmitate, and octadecyl stearate. These wax esters can be used alone or in admixture of two or more kinds.

Examples of the above-mentioned hydrocarbons include, for instance, hexane, heptane, octane, nonane, decane, undecane, dodecane, tridecane, tetradecane, pentadecane, hexadecane, heptadecane, octadecane, and the like. These hydrocarbons can be used alone or in admixture of two or more kinds.

Methods of including at least one substance selected from the group consisting of starting materials of an alcohol, alcohols, wax esters, and hydrocarbons which is present in a liquid form on the surfaces or within the pores of the hydrogenation catalyst, include, for instance, a method of immersing a hydrogenation catalyst in a container charged with the above substance in a liquid form prior to packing the hydrogenation catalyst in a reducing reactor; and a method of packing a hydrogenation catalyst in a reducing reactor, and thereafter feeding the above substance in a liquid form into the reducing reactor, without intending to limit the methods employed in the present invention thereto.

The amount of the above substance which is present on the surfaces or within the pores of the hydrogenation catalyst is not particularly limited. By including even a small amount of the above substance to be present in the hydrogenation catalyst, the lowering in the amount of the side-products contained in the formed alcohol, particularly in the amount of the formed hydrocarbons, can be attained. In order to sufficiently exhibit the effects attained by the inclusion of the substance, it is desired that the entire surfaces of the above-mentioned hydrogenation catalyst are coated by the above substance.

In addition to the feature of employing a hydrogenation catalyst in the present invention, in which at least one substance selected from the group consisting of starting materials of an alcohol, alcohols, wax esters, and hydrocarbons is present in a liquid form on surfaces or within pores of the hydrogenation catalyst, as the above-mentioned hydrogenation catalyst, another major feature of the present invention resides in that the temperature inside the above reducing reactor is at a temperature of not less than a dew point of the formed alcohol.

In other words, the active sites of the above-mentioned hydrogenation catalyst are present on the surfaces or within the pores of the hydrogenation catalyst. In this case, the hydrogenation catalyst is treated such that the above substance is previously present in a liquid form in the active sites prior to supplying the starting materials of an alcohol in the reducing reactor. Therefore, when the reduction reaction of the starting materials of an alcohol is carried out using the hydrogenation catalyst treated as described above, a reaction intermediate, a wax ester, is formed by liquid-phase reaction on the surfaces or within the pores of the hydrogenation catalyst at the initial stage of reaction. The formed wax ester is further hydrogenated by the above substance (liquid phase), to give an alcohol. In this case, since the temperature inside the reducing reactor is not less than a dew point of the formed alcohol, the alcohol which is included in the above substance (liquid phase) is entirely shifted towards the side of the vapor phase. By the shifting effects of the liquid phase to the vapor phase of the alcohol, the reaction equilibrium between the wax ester and the alcohol in the liquid phase is shifted towards the side of the alcohol formation. Therefore, the lowering of the amount of the wax ester can be attained, to an extent that the separation and removal of the wax ester are no longer necessitated.

In addition, in the vapor-phase region, the reaction for formation of an alcohol may take place. Since the reaction is a vapor-phase reaction, substantially no reaction intermediates, wax esters, are formed according to the above reaction equilibrium.

Furthermore, a wax ester having a high dew point selectively remains as a liquid on the surfaces or within the pores of the hydrogenation catalyst. Therefore, there is an advantage that when the temperature inside the reducing reactor is adjusted to a temperature of not more than a dew point of the wax ester contained in the hydrogenation catalyst, the surfaces or the pores of the hydrogenation catalyst are less likely to be in a dry state. As a result, it is made possible to avoid a contact of starting organic compounds and the formed compounds as liquid droplets with the catalyst as in the cases described in Japanese Patent Unexamined No. Hei 4-504408 and Japanese Patent Laid-Open No. Hei 7-188077. Therefore, as compared with the reaction system where the formed alcohol is easily reduced to the hydrocarbons, the amount of the formed side-products, particularly the formed hydrocarbons, can be lowered.

Here, the dew point of the wax esters which are present in alcohols and within the pores of catalysts can be obtained based on a known high-pressure vapor-liquid equilibrium calculation expression such as Soave-Redlich-Kwong (SRK) expression given below.

$$\phi_i^V Y_i \pi = \phi_i^L X_i \pi$$

$$\ln \phi_i = \frac{1}{RT} \int_V^\infty \left[ \left( \frac{\partial P}{\partial N_i} \right)_{T \cdot V \cdot N_j (j \ne i)} - \frac{RT}{V} \right] dV - \ln Z$$

$$P = \frac{RT}{V - b} - \frac{a(T)}{V(V + b)}$$

wherein $\Phi_i^V$ is a fugacity coefficient of component "i" in the vapor phase; $\Phi_i^L$ is a fugacity coefficient of component "i" in the liquid phase; $X_i$ is a composition of component "i" in the liquid phase; $Y_i$ is a composition of component "i" in the vapor phase; a(T) and b are respectively constants; P is a pressure; V is a volume; T is a temperature; Z is a compressibility factor; and R is a gas constant.

In addition, the above dew point can be calculated, together with the above SRK expression, by using a Kelvin equation disclosed by Zigmondy et al. (R. Zigmondy, Z. anorg. Chem., 71, 356(1911), which takes into consideration the state within the pores, expressed as follows:

$$\ln\left(\frac{P}{P_s}\right) = \frac{2\gamma M}{RT\rho r}$$

wherein P is a vapor pressure of a liquid whose concave surface has a radius r; $P_s$ is a vapor pressure of the liquid at a horizontal surface at the same temperature; $\gamma$ is a surface tension of the liquid; M is a molecular weight of the liquid; R is a gas constant; T is a temperature; and $\rho$ is a density of the liquid.

Incidentally, in Examples and Comparative Examples set forth below, the dew points are calculated based on the SRK equation.

In the present invention, alcohols are produced by the steps of continuously supplying and flowing the starting materials of an alcohol in a reducing reactor packed with a hydrogenation catalyst treated such that the above substance is present on the surfaces or within the pores of the hydrogenation catalyst in a liquid form, and carrying out catalytic reduction reaction using the hydrogenation catalyst. The reducing reactors which can be used in the catalytic reduction reaction are not particularly limited as to their model numbers as long as they are devices capable of continuously supplying and flowing the mixture of the starting materials of an alcohol and hydrogen gas. As for the reducing reactors, it is desired that a fixed bed reactor is used in order to smoothly proceed the reaction in the vapor phase. In this case, the hydrogenation catalyst is fixed inside the fixed bed reactor.

The starting materials of an alcohol to be supplied into the reducing reactor are pre-heated and vaporized as occasion demands. The pre-heating and vaporization mentioned above can be carried out by a known method utilizing a packed column or the like. In this case, a part or all the starting materials of an alcohol can be vaporized depending upon the reaction conditions in the reducing reactor.

Incidentally, when the starting materials of an alcohol are introduced in the reducing reactor containing the hydrogenation catalyst treated such that the above substance is present on the surfaces or within the pores of the hydrogenation catalyst, the temperature inside the above reducing reactor is set at a temperature of not less than a dew point of the formed alcohol. The reasons that the temperature inside the above reducing reactor is set at a temperature of not less than a dew point of the formed alcohol as mentioned above are as follows.

In other words, when the temperature inside the reducing reactor is lower than the dew point of the formed alcohol, the formed alcohol in the liquid phase is not shifted to the vapor phase. Therefore, as a result, large amounts of wax esters undesirably remain in the formed alcohol owing to the liquid-phase reaction equilibrium between the wax esters and the alcohols.

On the other hand, when the temperature inside the reducing reactor is adjusted to a temperature of not less than a dew point of the formed alcohol as in the present invention, a major portion of the formed alcohol in the liquid phase is shifted to a vapor phase. Therefore, the wax ester is apparently irreversibly hydrogenated to an alcohol, so that the amount of the wax ester is lowered to an extent that its separation and removal are not necessitated, to give a high-quality alcohol.

In order to adjust the temperature inside the reducing reactor to a temperature of not less than a dew point of the formed alcohol, for instance, the temperature, the pressure, and the molar ratio of hydrogen inside the reducing reactor can be desirably controlled.

From the aspects of maintaining reaction rates and being capable of easily vaporizing the starting materials of an alcohol and the formed alcohol, the temperature inside the reducing reactor is desirably not less than 100° C., more desirably not less than 150° C. In addition, from the aspect of selectivity of the formed alcohol, the temperature inside the reducing reactor is desirably not more than 300° C., more desirably not more than 270° C. A particularly desired temperature range is from 200° to 250° C.

From the aspects of maintaining reaction rates and being capable of having the reaction equilibrium shifted to the side of the formed product, the pressure inside the reducing reactor is desirably not less than 10 atm. From the aspects of being capable of easily vaporizing the starting materials of an alcohol and the formed alcohol, lowering the plant investment incurred by employing high-pressure equipments, and lowering the maintenance costs, the pressure inside the reducing reactor is desirably not more than 100 atm. A particularly desired pressure range is from 20 to 60 atm.

When the starting materials of an alcohol are continuously introduced into the reducing reactor, from the aspects of obtaining desired conditions of not less than a dew point of the alcohol without dramatically increasing the reaction temperature, the molar ratio of hydrogen in the reducing reactor, as defined as [hydrogen molecules/acyl group in the starting materials of an alcohol], is desirably not less than 100. In addition, from the aspect of limitations in the size of the equipments, the molar ratio of hydrogen is desirably not more than 1000. Incidentally, for instance, when a mixture of a methyl ester of a fatty acid is used as the starting material of an alcohol, the molar ratio of hydrogen is desirably from 100 to 1000, more desirably from 200 to 800.

By continuously supplying and flowing the starting materials of an alcohol in the reducing reactor and carrying out catalytic reduction reaction of the starting materials using a hydrogenation catalyst, an alcohol in which the amounts of the starting materials of an alcohol, the wax esters, and the hydrocarbons are lowered, to an extent that purification process is not necessitated, can be obtained.

EXAMPLES

The present invention will be explained in further detail by means of the following working examples, but the present invention is not restricted to these examples.

Examples 1 Through 8 and Comparative Examples 1 Through 4

A reducing reaction tower with an inner diameter of 25 mm and a height of 2 m was packed with 500 ml of a Cu—Cr catalyst ("N202D" manufactured by NIKKI CHEMICAL Co., Ltd.) formed in a rod shape with a diameter of 3 mm, and the catalyst was reduced to be activated by a known reducing method using nitrogen gas containing 5 to 60% by volume of hydrogen gas.

Thereafter, the hydrogenation reaction was carried out by continuously supplying and flowing one of the starting materials of an alcohol selected from starting materials A of an alcohol, starting materials B of an alcohol, and the starting material only composed of methyl laurate (simply referred to as "C12ME") having the composition shown in Table 1 through the reducing reaction tower together with hydrogen gas under the reaction conditions shown in Table 2.

TABLE 1

| Starting Materials of Alcohols | Kinds of Starting Materials of Alcohols (Parts by weight) | |
| --- | --- | --- |
| | A | B |
| Methyl Caprylate | 4.6 | 7.3 |
| Methyl Caprate | 4.1 | 6.4 |
| Methyl Laurate | 50.9 | 75.0 |
| Methyl Myristate | 16.0 | 11.3 |
| Methyl Palmitate | 7.6 | — |
| Methyl Stearate | 16.8 | — |

Here, in Comparative Example 1, the vaporous starting materials were supplied after sufficiently drying the surfaces of the hydrogenation catalyst. On the other hand, in all of the remaining Examples and Comparative Examples, the hydrogenation catalysts packed in the reducing reaction tower were sufficiently coated with the starting materials of an alcohol in a liquid form supplied in the reaction prior to the reduction reaction.

Incidentally, the procedure of treating the hydrogenation catalyst such that the above substance in a liquid form is present on the surfaces or within the pores of the hydrogenation catalyst was carried out by packing the hydrogenation catalyst in the reducing reaction tower, and thereafter feeding starting materials of an alcohol as the above substance.

The wax ester and the hydrocarbons were quantitatively analyzed by diluting a sample collected at the outlet of the reducing reaction tower with a solvent (ethanol), and measuring with a capillary gas chromatography ("GC-14A" manufactured by Shimadzu Corporation, column: "ULTRA#1" manufactured by HEWLETT PACKARD).

Incidentally, in Table 2, the term "LHSV" stands for "liquid hourly space velocity" which is a value obtained by dividing the volume flow rate of the starting materials per unit time by the volume of the reactor.

products, hydrocarbons, are extremely large, though the amount of the wax ester included in the formed alcohol is lowered by the reaction equilibrium in the vapor-phase reaction, to an extent that separation is not necessitated. This is presumably owing to the fact that in the vapor-phase reaction where the hydrogenation catalyst is not covered by the liquid at all, not only the main reaction but also the side reaction progress.

It is clear from the above that when a large amount of the hydrocarbons is included in the formed alcohol, there are brought about a lowered yield of an alcohol, a lowered alcohol quality, and, moreover, the purification process is necessitated.

In the cases of Comparative Examples 2 to 4 where the temperature inside the reducing reaction tower is not more than a dew point of the formed alcohol, the amount of the reaction intermediate, the wax ester, included in the formed alcohol is large, thereby necessitating the separation of the wax ester from the aspect of alcohol quality control. This is presumably owing to the fact that the evaporation of the formed alcohol to the side of the vapor phase is not sufficient, so that the reaction equilibrium in the liquid phase is not sufficiently shifted to the side of the alcohol formation.

In Examples 1 to 8, by sufficiently coating the hydrogenation catalyst with liquid methyl ester prior to the hydrogenation reaction, the state of coating the surfaces of the above-mentioned hydrogenation catalyst with the methyl ester can be maintained even after the reaction progresses. As a result, the reaction selectivity can be remarkably improved, and the amount of the formed hydrocarbon is lowered, as well as the amount of the wax ester is lowered. Therefore, when the formed alcohol is used, for instance, in starting materials of detergents, the separation and removal processes of the wax ester from the formed alcohol are not necessitated.

In addition, in Examples 1 to 8, after the termination of reaction, when the hydrogenation catalyst is taken out from

TABLE 2

| | | Reaction Conditions | | | Dew | | Amount of Impurity in | | |
| --- | --- | --- | --- | --- | --- | --- | --- | --- | --- |
| Kinds of Starting Materials of Alcohol | Reaction Pressure (atm.) | Reaction Temp. (°C.) | Molar Ratio of Hydrogen (−) | LHSV (1/Hr) | Dew Point of Alcohol (°C.) | Point of Wax Ester (°C.) | Formed Alcohol (% by weight) | | |
| | | | | | | | Unreacted Ester | Wax Ester | Hydro-carbons |
| Example Nos. | | | | | | | | | |
| 1 | B | 40 | 220 | 200 | 0.5 | 204 | 311 | 0.12 | 0.14 | 0.14 |
| 2 | B | 50 | 220 | 200 | 0.5 | 209 | 318 | 0.10 | 0.12 | 0.13 |
| 3 | B | 60 | 220 | 200 | 0.5 | 213 | 324 | 0.08 | 0.10 | 0.11 |
| 4 | B | 40 | 220 | 300 | 0.5 | 194 | 297 | 0.14 | 0.11 | 0.17 |
| 5 | C12ME | 40 | 220 | 200 | 0.5 | 197 | 307 | 0.10 | 0.16 | 0.16 |
| 6 | A | 40 | 220 | 500 | 0.25 | 219 | 293 | 0.11 | 0.36 | 0.14 |
| 7 | A | 50 | 220 | 600 | 0.25 | 219 | 292 | 0.10 | 0.32 | 0.13 |
| 8 | A | 40 | 220 | 600 | 0.25 | 215 | 286 | 0.12 | 0.30 | 0.15 |
| Comparative Example Nos. | | | | | | | | | |
| 1 | B | 40 | 205 | 485 | 0.25 | 182 | 280 | 2.06 | 0.05 | 1.66 |
| 2 | A | 50 | 220 | 400 | 0.25 | 228 | 308 | 0.09 | 1.09 | 0.12 |
| 3 | A | 60 | 220 | 200 | 0.25 | 250 | 330 | 0.07 | 1.64 | 0.10 |
| 4 | A | 50 | 220 | 400 | 0.50 | 228 | 308 | 0.18 | 1.60 | 0.11 |

It is clear from Table 2 that when the reaction is carried out under the conditions that the above substance is not present in a liquid form in the hydrogenation catalyst (Comparative Example 1), the amounts of the formed sidethe reaction tower, the surfaces of the hydrogenation catalyst are coated with the liquid, and when the coated hydrogenation catalyst is washed with a solvent. The resulting washing liquid is analyzed by capillary gas chromatography in the same manner as above, as a result, it is confirmed that a wax ester is present within the pores of the above-mentioned hydrogenation catalyst.

As described above, in the methods of Examples 1 to 8, the liquid, such as an alcohol, is present on the surfaces or within the pores of the hydrogenation catalyst, and the temperature inside the reducing reaction tower is adjusted to a temperature of not less than a dew point of the formed alcohol. Therefore, there can be obtained an alcohol, in which the amounts of the reaction intermediate, the wax ester, and the side-products, the hydrocarbons, remaining in an alcohol can be lowered, to an extent that purification process, such as distillation, is not necessitated.

According to the method for producing an alcohol of the present invention, it is made possible to carry out the method of producing an alcohol without involving such complicated processes, such as separation of the starting materials depending upon the chain length at the stage prior to the hydrogenation reaction. Even in cases where the reaction pressure is low, the reactivity and the selectivity are excellent.

In other words, the amounts of the starting materials of an alcohol, the reaction intermediate, the wax ester, and the side-products, the hydrocarbons, remaining unreacted in the alcohol are lowered, to an extent that the purification process, such as distillation, is not necessitated, so that effects in a remarkable improvement in alcohol yields can be exhibited.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing an alcohol comprising the steps of:

continuously supplying and flowing starting materials of an alcohol in a reducing reactor; and carrying out catalytic reduction reaction of the starting materials with hydrogen gas in the presence of a hydrogenation catalyst, wherein said catalytic reduction reaction of the starting materials is carried out under temperature conditions of not less than a dew point of the resulting alcohol, and wherein said starting materials of an alcohol are brought in contact with hydrogen gas in the presence of a hydrogenation catalyst, in which at least one substance selected from the group consisting of starting materials of an alcohol, alcohols, wax esters, and hydrocarbons is present in a liquid form on a surface or within pores of the hydrogenation catalyst.

2. The method according to claim 1, wherein prior to the step of supplying and flowing the starting materials of an alcohol in the reducing reactor, said hydrogenation catalyst is treated such that at least one substance selected from the group consisting of starting materials of an alcohol, alcohols, wax esters, and hydrocarbons is present in a liquid form on a surface or within pores of the hydrogenation catalyst.

3. The method according to claim 1 or 2, wherein the temperature inside the reducing reactor is adjusted to a temperature of not more than a dew point of the wax esters present on a surface or within pores contained in the hydrogenation catalyst.

4. The method according to any one of claims 1 to 3, wherein the starting materials of an alcohol are a fatty acid ester.

5. The method according to claim 4, wherein the fatty acid ester is derived from coconut oil, palm oil, or palm kernel oil.

6. The method according to any one of claims 1 to 5, wherein a fixed bed reactor containing a hydrogenation catalyst fixed inside the reducing reactor is used as the reducing reactor.

7. The method according to any one of claims 1 to 6, wherein the temperature inside the reducing reactor is from 100° to 300° C., and the pressure inside the reducing reactor is from 10 to 100 atm.

* * * * *